United States Patent [19]

Baszczynski et al.

[11] Patent Number: 5,659,026
[45] Date of Patent: Aug. 19, 1997

[54] ALS3 PROMOTER

[75] Inventors: Chris Baszczynski, Urbandale; Eric Barbour, Des Moines, both of Iowa; Brian Miki, Ottawa, Canada

[73] Assignee: Pioneer Hi-Bred International, Des Moines, Iowa

[21] Appl. No.: 409,297

[22] Filed: Mar. 24, 1995

[51] Int. Cl.$^6$ .............................. C12N 15/29; C12N 5/04; C12N 15/82; A01H 5/00
[52] U.S. Cl. ...................... 536/24.1; 536/23.6; 435/69.1; 435/70.1; 435/172.3; 435/320.1; 435/418; 435/419; 800/205
[58] Field of Search .............................. 536/24.1, 23.6; 435/69.1, 70.1, 172.3, 240.4, 320.1; 800/205

[56] References Cited

FOREIGN PATENT DOCUMENTS

| 0 559 603 A2 | 9/1993 | European Pat. Off. |
| WO 9607746A1 | 3/1996 | WIPO. |

OTHER PUBLICATIONS

Rutledge, et al. "Molecular characterization and genetic origin of the Brassica napus acetohydroxyacid synthase multigene family", *Mol Gen Genet*, 229:31–40 (1991).
Ouellet, et al. "Members of the acetohydroxyacid synthase multigene family of Brassica napus have divergent patterns of expression", *The Planet Journal*, 2(3):321–330 (1992).
Gabard, et al. "Cross-Resistance to Short Residual Sulfonylurea Herbicides in Transgenic Tobacco Plants", *Plant Physiol.*, 91:574–580 (1989).
Wiersma, et al. "Isolation, expression and phylogenetic inheritance of an acetolactate synthase gene from Brassica napus", *Mol Gen Genet*, 219:413–420 (1989).
Miki, et al. "Transformation of Brassica napus canola cultivars with Arabidopsis thaliana acetohydroxyacid synthase genes and analysis of herbicide resistance", *Theor Appl Genet*, 80:449–458 (1990).
Hattori, et al. "An acetohydroxy acid synthase mutant reveals a single site involved in multiple herbicide resistance", *Mol. Gen Genet*, 246:419–425 (1995).

Brandle et al. A Comparison of Two Genes for Sulfonylurea Herbicide Resistance in Transgenic Tobacco Seedlings, *Crop Science* 34:226–229 (1994).
Tourneur, et al. *Plant Science*, vol. 88, pp. 159–168, 1993 "Over-expression of acetolactate synthase confers resistance to valine in transgenic tobacco".
Barbour, et al. Proceedings of the 1993 Annual Meeting of the CSPMB, p. 43, 1993 "Characterization of a B. Napus ALSIII gene and expression in transgenic plants".
Rutledge, et al. *Mol. Gene Genet.*, vol. 229, pp. 31–40, 1991 "Molecular characterization and genetic origin of the Brassica napus acetohydroxyacid synthase multigene family".
Odell, et al. *Plant Physiol.*, vol. 94, pp. 1647–1654, 1990 "Comparison of increased expression of wild-type and herbicide-resistant acetolactate synthase genes in transgenic plants, and indication of posttranscriptional limitation on enzyme activity".
Wiersma, et al. *Mol. Gen Genetics*, vol. 219, pp. 413–420, 1989 "Isolation, expression and phylogenetic inheritance of an acetolactate synthase gene from Brassica napus".
Barbour, et al. *J. Cell Biochem. Suppl.*, p. 204, 1992 Abstract "Isolation and characterization of B Napus mutant ALS gene and expression in transgenic plants".

*Primary Examiner*—David T. Fox
*Attorney, Agent, or Firm*—Foley & Lardner

[57] ABSTRACT

The Brassica ALS3 promoter is operably linked to a foreign structural gene to provide high level, and generally constitutive or tissue general expression of the structural gene in transformed plants. The Brassica ALS3 promoter exhibits a non-tissue-preferred mode of expression at a level comparable to, and in some cases higher than, the widely used CaMV 35S promoter. Accordingly, DNA constructs comprising the Brassica ALS3 promoter operably linked to any number of different gene coding regions can be used for constitutive and tissue-general expression of the gene in transformed plants. The Brassica ALS3 promoter is used to direct expression of agronomically important genes and selectable marker genes.

11 Claims, 12 Drawing Sheets

FIG. 1A

```
-1059        TCTAGATTAA CATATGCGAC CACTCAGGTT AATAATTCTC CCAAATAAC
             ----- 
             Xbal
-1009   TACATTGGTA TGAAGATTAT GTCTAAATCA AACATAAAAT CGACTCCAA
-959    TACGAACCCA CAAACTTACA AGTAAATCAA ACATAAAATT TATCTGCATC
-909    CGACTATGTC TACGCCATTG TTTCACCACT CACCAATTAT AGAGGGACAA
-859    ACCTACAGAT CATACTATAT CTAACAGATT TCAACCCCTA AGCAATTCAC
-809    AGAATTGACA TGGACATAGC TAGAGCAAAC CTGCATGATG AAAGAAGGGC
-759    ACCCACAGTG GCGGAAAAAG ATGAACTTTT GACAATACAC ATTGACAAGA
-709    TTGTATGAAG TGGGGTTATA AATTCATTGC AATGCAATCA TATCTATCAT
-659    CACCAGTTCA TAATTGACTG GATCCGAATG AACATAAGAT GCTCTACAGTG
-609    TCGAGACACA ATACTTTAGT CATAATGTTT CTCATTATCA AGTACAGGTA
-559    TTTCTACTTT AAACTTATAT TATAAGCAAG TATTACAAAT AATGAAATAA
```

FIG. 1B

```
-509  AGACTATGTT TCCTGTTTT AGATGTTTCG ATCTTCATAT TTTAACCAAT

-459  CGTCTTCATT ATTGCAAGAA ACACAATTTC CTAACTCCTG TAACACTCCT

-409  TATAAAAATA TATGACATAT GAAACGGAGC GGAGGCTTGC AGTAGACGTA

-359  ACAACATTTT AAAATTGAAC AAGTATTGC TTAAAAAATA GAATTTGAAG

-309  GCCTTCTAAG CTGAACATAA AATAAAATTA ACACAAAATT ATATCTTTCA

-259  TCACAACCAA CTGAACATAA AATAAAATTA ACACAAAATT ATATCTTTCA

-209  TAAAACCGA TACATCAAAT TCCGGCGGTA GGCGGGACCC TCCCTAGTAA

-159  TTAATACAGT AAAGAAAAGA CCAAACAAAC AAAAATCATA TTCCAAGGGT

-109  ATTTTCGTAA ACAAACAAAA CCCTCACAAG CCTCGTTTTA TAAAAACGAT

-59   TCACGTTCAC AAACTCATTC ATCATCTCTC TCTCATTTCT CTCTCTCT

-9    CATCTAACC ATGG
                +1
                Ncol
```

FIG. 2A

```
Xbal      Ndel         Ddel                                           Msll
TCTAGATTAACATATGCGACCACTCAGGTTAATAATTCTCCAAATAACATACATTGGTATGAAGATTA
TGTCTAAATCAAACATAAAATGACTCCAAATCGAACCACAAACTTACAAGTAAATCAAACATAAAA
       Fokl  Aspl Accl
TTTATCTGCATCGACTATGTCTACGCCATTGTTCCACTCACCAATTATAGAGGACAAACCTACA
Dpnl                                        Ddel                    Alul
GATCATACTATATCTAACAGATTTCAACCCCTAAGCAATTCACAGAATTGACATGACATAGCTAGAGC
BspMI         Banl
AAACCTGCATGATGAAAAGAGGCACCCAGTGGCGAAAAAGATGAACTTTGACATATACACATTGA
                                            Msll
CAAGATTGTATGAAGTGGGTTATAAATTCATTGCAATGCAATCTATCATCCAGTTCATAAT
  Dpnl                                Aflllll
  BamHI                               Nspl
  Bstl
TGACTGGATCGAATGAACATAAGAGTCTCTACATGTCGAGACACAATACTTTAGTCATAATGTTTCTC
     Rsal              Dral
ATTATCAAGTACAGTATTCTACTTTAAACTTATATTATAAGCAAGTATTACAAATAATGAAATAAAG
```

FIG. 2B

```
                              Bbsl
      Dpnl
ACTATGTTTTCCTGTTTAGAGTTTGATCTTCATATTTAACCAATGTCTTCATTATTGCAAGAAA Ndel
CACAATTCCTACTCCTGTAACTCCTTATAAAATATATGACATATGAAACGGAGCGGAGGCTTGC
                                                       Haelll
                                                       Stul
              Dral                    Xmnl        Ddel
     Accl
AGTAGACGTAACAACATTTAAATTGAACAAGTATTGCTTAAAAATAGAATTTGAAGGCCTTCTAA Asul
GTTTAATAAATTAACACTTAAACACTTAAATTATCACCCTCACAACTGAACATAAAATAAAAT Hhal   Hhal Avall
TAACACAAATTATATCTTTCATAAACCGATACATCAAATTCCGGGTAGGCGGACCCTCCCTAG
Asnl                                              Styl
TAATTAATACAGTAAAAAGACCAACAAAAATCATATTCCAAGGGTATTTCGTAAACAAAC
                              Tfll
AAAACCCTCACAGCCTGCGTTTATAAAAGATTCAGTTCACAACTCATTCATCTCTCTCTCA
         Ncol
         Styl
TTTCTCTCTCTCTCTCATCTAACCATGG
```

ALS3 PROMOTER

BACKGROUND OF THE INVENTION

I. Field of the Invention

The present invention relates to a novel ALS3 promoter which generally drives constitutive and generally non-tissue-preferred expression of operably linked foreign genes in transformed plants. In particular, this invention is directed to DNA constructs in which a Brassica ALS3 promoter is operably linked to a foreign structural gene, and to using the DNA construct to produce, in a transformed plant, a protein which is encoded by the structural gene. The Brassica ALS3 promoter is used to direct expression of agronomically important genes and selectable marker genes.

II. Background

Acetolactate synthase (ALS), which is also known as acetohydroxy acid synthase (AHAS), catalyses the first step in the biosynthesis of the branched chain amino acids leucine, isoleucine and valine. It has also been shown to be the site of action of sulfonylurea and imidazolinone based herbicides. See, for example, Chaleff, R. S. and C. J. Mauvais, Science 224:1443 (1984) and Shaner et al., Plant Physiol. 76:545 (1984). A number of different ALS genes from Brassica napus have been cloned and characterized. See, for example Wiersma et al., Mol. Gen. Genetics 219:413 (1989) and Rutledge et al., loc. cit. 229:31 (1991).

Rutledge et al. (1991) reported that the B. napus rapeseed cultivar Topas contains an ALS multigene family comprised of five genes. DNA sequence analysis of the structural genes revealed that the ALS1 and ALS3 genes shared extensive sequence homology. In contrast, the ALS2 gene has diverged significantly from the ALS1 and ALS3 genes and has unique features in the coding region of the mature polypeptide, transit peptide and upstream non-coding region. The ALS2 gene therefore may encode a polypeptide with a distinct function from that of ALS1 and ALS3. The ALS4 and ALS5 genes have interrupted coding regions and therefore may be defective.

Experiments conducted with the promoter of the Arabidopsis thaliana ALS gene revealed that the A. thaliana ALS promoter is significantly less effective in driving gene expression than the CaMV 35S promoter. Odell et al., Plant Physiol. 94(4):1647–1654 (1990) replaced the A. thaliana ALS promoter with the CaMV 35S promoter and observed a 25-fold increase in the level of ALS mRNA accompanied by a 2-fold increase in ALS enzyme level and a 3-fold increase in sulfonylurea tolerance. These observations indicate that the ALS gene is regulated post-transcriptionally and that the A. thaliana ALS promoter is significantly less effective in driving gene expression than the CaMV 35S promoter.

The number of isolated and characterized constitutive generally non-tissue-preferred plant promoters available for expression of foreign proteins in transgenic plants is very limited. Well known examples of promoters with constitutive and tissue generated expression patterns include those associated with the CaMV 35S, Agrobacterium nopaline synthase, and maize ubiquitin genes. See Odell et al., Plant Mol. Biol. 10(3):263–272 (1988), Herrera-Estrella et al., Nature 303:209–213 (1983) and Fox et al., Va. J. Sci. 43(2):287 (1992).

There is a critical need for a broader repertoire of strong constitutive and generally non-tissue-preferred plant promoters. A broader array of constitutive and generally non-tissue-preferred plant promoters that are expressed at high levels, that is, that drive expression of operably linked genes at a level comparable to the CaMV 35S promoter, would allow the genetic engineer to analyze the relative strengths of the available promoters and select promoters that provide the required level of expression of foreign genes in transformed plants. A selected promoter might provide optimum levels of expression for the first gene but may be either too strong or too weak for use in driving the expression of a second gene. Consequently, additional constitutive and tissue general promoters are needed to optimize foreign gene expression in plants.

There is also a need for additional strong constitutive and generally non-tissue preferred promoters for construction of plants transformed with multiple foreign genes. Numerous difficulties have arisen when two or more different genes are introduced into a plant wherein each of the genes are operably linked to the same or similar promoters. Some of these difficulties include (1) gene inactivation; (2) recombination as a result of pairing along homologous regions within the nucleotide sequence of the promoter leading to cross-over events and loss of the intervening region prior, or subsequent to, integration; and (3) competition among different copies of the same promoter region for binding of promoter-specific transcription factors or other regulatory DNA-binding proteins. A need therefore exists for a broader repertoire of strongly constitutive and tissue general promoters to be used for expression of foreign genes in transformed plants.

SUMMARY OF THE INVENTION

Accordingly, it is an object of the present invention to provide a strong, constitutive promoter which can effect high level, generally non-tissue-preferred expression of an operably linked, foreign genes in transformed plants.

It is another object of the present invention to add to the limited repertoire of generally non-tissue-preferred promoters available for the transformation of plants with multiple genes.

In achieving these and other objects, there has been provided, in accordance with one aspect of the present invention, an isolated DNA molecule comprising a promoter operably linked to a foreign structural gene, wherein said promoter comprises a nucleotide sequence corresponding to the sequence of a polynucleotide from the group consisting of (1) a XbaI/NcoI fragment 5-prime to the Brassica napus ALS3 structural gene or (2) a nucleotide sequence that has substantial sequence similarity with said XbaI/NcoI fragment. Other objects of the present invention include providing an isolated DNA molecule wherein the promoter is operably linked to an agronomically important gene or a selectable marker gene, an isolated DNA that is part of an expression vector and an expression vector carrying the isolated DNA molecule that is present in a transformed host.

It is another object of the present invention to provide an isolated DNA molecule comprising a promoter operably linked to a foreign structural gene, wherein said promoter comprises a nucleotide sequence corresponding to the sequence of a polynucleotide from the group consisting of (1) SEQ ID NO: 1 or (2) a nucleotide sequence that has substantial sequence similarity with SEQ ID NO: 1. Other objects of the present invention include providing an isolated DNA molecule wherein the promoter is operably linked to an agronomically important gene or a selectable marker gene, an isolated DNA that is part of an expression vector and an expression vector carrying the isolated DNA molecule that is present in a transformed host.

Another object of the present invention is to provide a method of using an ALS3 promoter to produce a foreign protein in a transformed host plant, comprising the steps of (1) constructing an expression vector comprising a promoter operably linked to a foreign structural gene, wherein the promoter comprises a nucleotide sequence corresponding to the sequence of a polynucleotide from the group consisting of (a) a XbaI/NcoI fragment 5-prime to the *Brassica napus* ALS3 structural gene or (b) a nucleotide sequence that has substantial sequence similarity with said XbaI/NcoI fragment; and (2) transforming a host.

Yet another object of the present invention is to provide a method of using an ALS3 promoter to produce a foreign protein in a transformed host plant, comprising the steps of (1) constructing an expression vector comprising a promoter operably linked to a foreign structural gene, wherein said promoter comprises a nucleotide sequence corresponding to the sequence of a polynucleotide from the group consisting of (a) SEQ ID NO: 1 or (b) a nucleotide sequence that has substantial sequence similarity with SEQ ID NO: 1; and (2) transforming a host.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A–B present the nucleotide sequence [SEQ ID NO: 1] of a 1063 bp XbaI/NcoI fragment that comprises the promoter 5-prime to the *B. napus* ALS3 wild type structural gene. The XbaI and NcoI restriction sites are underlined. The ATG start codon is found within the NcoI restriction site.

FIG. 2A–B presents a restriction map of a 1063 bp XbaI/NcoI fragment which comprises the *B. napus* ALS3 wild type structural gene (SEQ ID NO:1).

DETAILED DESCRIPTION OF THE INVENTION

I. Definitions

Figure 3:
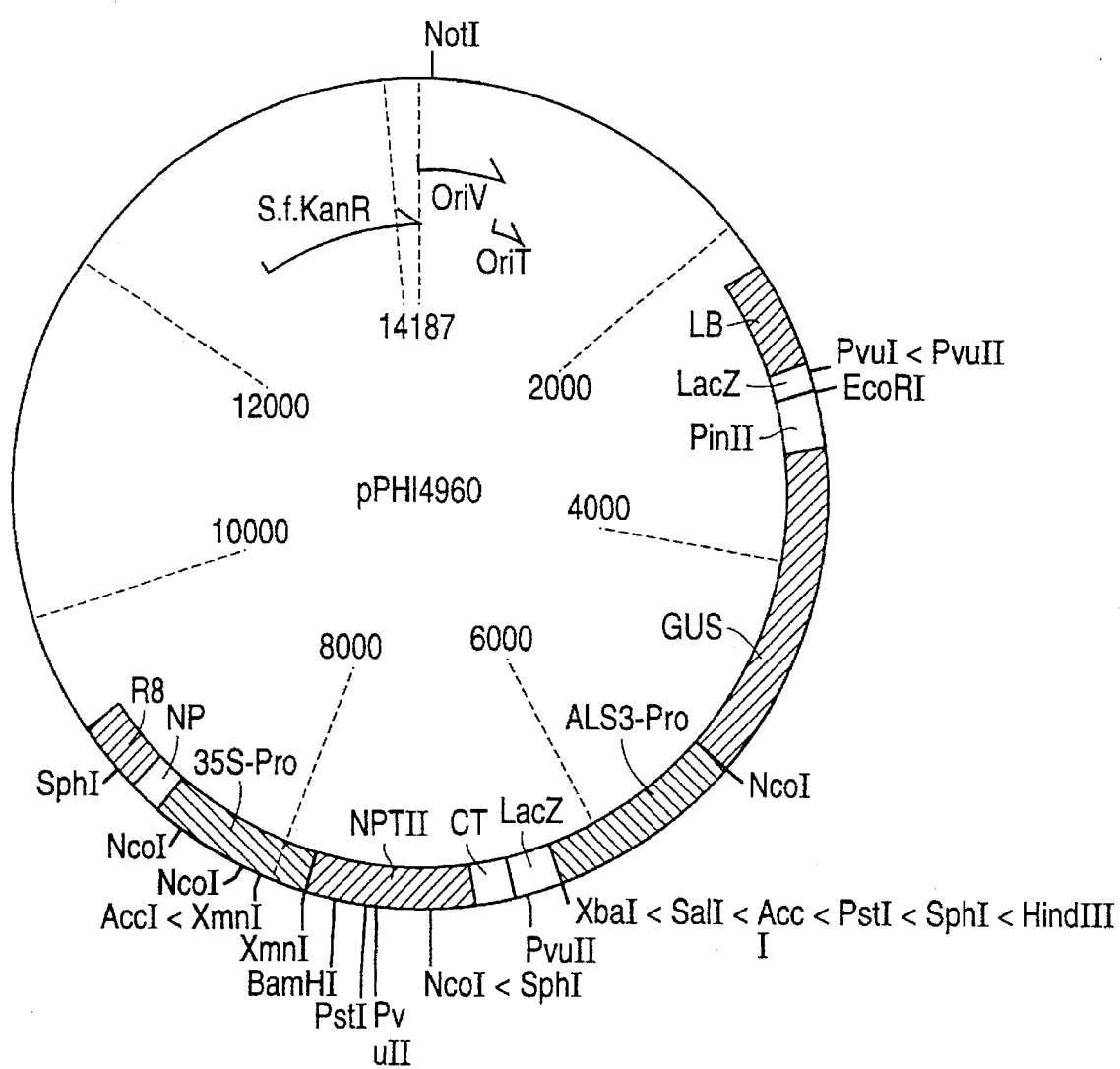
FIG. 3 presents a map of pPHI4960, a binary vector containing the *B. napus* ALS3 promoter (ALS3-Pro) driving uidA (GUS) gene expression. Plasmid pPHI4960 was used to transform canola and sunflower. LB and RB represent the left and right borders, respectively, of the Agrobacterium Ti plasmid T-DNA region. The region between the left and right borders also includes a CaMV 35S promoter (35S-Pro) driving expression of the NPTII gene for kanamycin selection of transformed plants.

In the description that follows, a number of terms are used extensively. The following definitions are provided to facilitate understanding of the invention.

A structural genes is a DNA sequence that is transcribed into messenger RNA (mRNA) which is then translated into a sequence of amino acids characteristic of a specific polypeptide.

A promoter is a DNA sequence that directs the transcription of a structural genes. Typically, a promoter is located in the 5' region of a gene, proximal to the transcriptional start site of a structural genes. If a promoter is an inducible promoter, then the rate of transcription increases in response to an inducing agent. For example, a promoter may be regulated in a tissue-specific manner such that it is only active in transcribing the associated coding region in a specific tissue type(s) such as leaves, roots or meristem.

In contrast, the rate of transcription is not generally regulated by an inducing agent if the promoter is a constitutive promoter. The promoter may be tissue-general, also known as non-tissue-preferred, such that it is active in transcribing the associated coding region in a variety of different tissue types.

A core promoter contains essential nucleotide sequences for promoter function, including the TATA box and start of transcription. By this definition, a core promoter may or may not have detectable activity in the absence of specific sequences that may enhance the activity.

An isolated DNA molecule is a fragment of DNA that is not integrated in the genomic DNA of an organism. For example, the promoter of the ALS3 gene is a DNA fragment that has been separated from the genomic DNA of *Brassica napus*.

Complementary DNA (cDNA) is a single-stranded DNA molecule that is formed from an mRNA template by the enzyme reverse transcriptass. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

To operably link one nucleotide sequence to another refers to joining two heterologous DNA fragments to produce a chimeric DNA construct that has biological activity. For example, an isolated DNA fragment comprising a promoter from a first genes, such as the ALS3 genes, is operably linked to an isolated DNA fragment comprising the structural genes from a second heterologous genes. The resulting chimeric DNA construct is functional when the AL3 promoter is shown to initiate transcription of the heterologous structural genes.

The term expression refers to the biosynthesis of a gene product. For example, in the case of a structural gene, expression involves transcription of the structural genes into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a genes that is expressed in a host cell. Typically, genes expression is placed under the control of certain regulatory elements, including constitutive or inducible promoters, tissue-specific regulatory elements, and enhancers. Such a genes is said to be "operably linked to" the regulatory elements.

A foreign gene refers in the present description to a DNA sequence that is operably linked to at least one heterologous regulatory element. For example, any genes other than the ALS3 structural genes is considered to be a foreign genes if the expression of that genes is controlled by the ALS3 promoter.

A recombinant host may be any prokaryotic or eukaryotic cell that contains either a cloning vector or expression vector. This term also includes those prokaryotic or eukaryotic cells that have been genetically engineered to contain the cloned genes(s) in the chromosome or genome of the host cell.

A transgenic plant is a plant having one or more plant cells that contain an expression vector.

In eukaryotes, RNA polymerass II catalyzes the transcription of a structural genes to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense genes. Antisense RNA molecules are capable of binding to mRNA molecules, resulting in an inhibition of mRNA translation.

A first nucleotide sequence has substantial sequence similarity to the nucleotide sequence of FIG. 1 [SEQ. ID NO: 1] if the former sequence share a similarity of at least 65% with the FIG. 1 sequence and is a constitutive promoter active in directing the transcription of an operably linked foreign structural genes in plants. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO© BLAST Network Service. See Altschul et al., *J. Mol. Biol.* 215:403 (1990). Also, see Pasternak et al., "Sequence Similarity Searches, Multiple Sequence Alignments, and Molecular Tree Building," in METHODS IN PLANT MOLECULAR BIOLOGY AND BIOTECHNOLOGY, Glick et al. (eds.), pages 251–267 (CRC Press 1993). Promoter activity of the isolated nucleotide sequence can be assayed by means of fusing the nucleotide sequence to a coding region of a foreign reporter gene. Promoter activity is measured by assaying reporter expression. See, for example, An etal., "Techniques for Isolating and Characterizing Transcription Promoters, Enhancers, and Terminators," in METHODS IN PLANT MOLECULAR BIOLOGY AND BIOTECHNOLOGY, Glick et al. (eds.), pages 155–166 (CRC Press, 1993).

II. Cloning of ALS3 Promoters

A 1063 bp XbaI/NcoI fragment comprising the promoter region of the ALS3 gene from wild type *Brassica napus* was cloned into pGEM5 (Promega Corporation, Madison, Wis.) and characterized. The nucleotide sequence of the 1063 bp XbaI/NcoI fragment was determined by the dideoxy sequencing protocol. Sanger et al., *Proc. Nat'l Acad. Sci. USA*, 74:5463 (1977). The nucleotide sequence of the 1063 bp XbaI/NcoI fragment is shown in FIG. 1 [SEQ ID NO: 1] and a detailed restriction map of this same fragment is shown in FIG. 2.

Other ALS3 promoters having substantial sequence similarity with the nucleotide sequence shown in FIG. 1 can be cloned by conventional methods. Oligonucleotides of defined sequence are chemically synthesized. Itakura et al., *Annu. Rev. Biochem.* 53:323 (1984). Numerous automated and commercially available DNA synthesizers are currently available. The probe can be a single and relatively short oligonucleotide of defined sequence, pools of short oligonucleotides whose sequences are highly degenerate or pools of long oligonucleotides of lesser degeneracy. Sambrook et al., *Molecular Cloning: A Laboratory Manual*, 2nd ed. (Cold Spring Harbor Press, Cold Spring Harbor, N.Y. 1989).

The oligonucleotide hybridization probes based on SEQ ID NO: 1 are labeled, for example radio labeled, by conventional methods and used to detect related nucleotides sequences in Brassica genomic libraries by means of DNA hybridization. See, for example, Sambrook supra.

A plant genomic DNA library can be prepared by means well-known in the art. See, for example, Slightom et al. "Construction of λ Clone Banks," in METHODS IN PLANT MOLECULAR BIOLOGYAND BIOTECHNOLOGY, Glick et al. (eds.), pages 121–146 (CRC Press, 1993). Genomic DNA can be isolated from Brassica tissue, for example, by lysing plant tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient. Ausubel et al. (eds.), CURRENT PROTOCOLS IN MOLECULAR BIOLOGY, pages 2.3.1–2.3.3. (1990).

DNA fragments that are suitable for the production of a genomic library can be obtained by the random shearing of genomic DNA or by the partial digestion of genomic DNA with restriction endonucleases. See, for example, Ausubel et al. supra, at pages 5.3.2–5.4.4, and Slightom et al., supra.

Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are disclosed by Slightom et al., supra, and are well-known in the art. Also see Ausubel et al., supra, at pages 3.0.5–3.17.5.

A library containing genomic clones is screened with DNA hybridization probes based on the nucleotides sequence of the ALS3 promoter shown in FIG. 1 [SEQ ID NO: 1] using standard techniques. See, for example, Ausubel et al., supra, at pages 6.0.3–6.6.1; Slightom et al., supra.

III. Characterization of ALS3 Promoters

Genomic clones can be analyzed using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel et al., supra, at pages 4.8.1–4.8.5; Walmsley et al., "Quantitative and Qualitative Analysis of Exogenous Gene Expression by the S1 Nuclease Protection Assay," in METHODS IN MOLECULAR BIOLOGY, VOL. 7: GENE TRANSFERAND EXPRESSION PROTOCOLS, Murray (ed.), pages 271–281 (Humana Press Inc. 1991). Structural analysis can be combined with functional analysis for a complete characterization of the promoter region.

The general approach of such functional analysis involves subcloning fragments of the genomic clone into an expression vector which contains a reporter gene, introducing the expression vector into various plant tissues, and assaying the tissue to detect the transient expression of the reporter gene. The presence of a constitutive, tissue-general promoter is verified by the observation of reporter gene expression in diverse plant tissues including roots, stems or leaves.

Methods for generating fragments of a genomic clone are well-known. Preferably, enzymatic digestion is used to form nested deletions of genomic DNA fragments. See, for example, Ausubel et al., supra, at pages 7.2.1–7.2.20; An et al., supra.

Alternatively, DNA that resides "upstream," or 5'-ward, of the transcriptional start site can be tested by subcloning a DNA fragment that contains the upstream region, digesting the DNA fragment in either the 5' to 3' direction or in the 3' to 5' direction to produce nested deletions, and subcloning the small fragments into expression vectors for transient expression.

The selection of an appropriate expression vector will depend upon the method of introducing the expression vector into host cells. Typically, an expression vector contains: (1) prokaryotic DNA elements coding for a bacterial replication origin and an antibiotic resistance marker to provide for the growth and selection of the expression vector in the bacterial host; (2) eukaryotic DNA elements that control initiation of transcription, such as a promoter; (3) DNA elements that control the processing of transcripts, such as a transcription termination/polyadenylation sequence; and (4) a reporter gene that is operably linked to the DNA elements that control transcription initiation. Useful reporter genes include β-glucuronidase, β-galactosidase, chloramphenicol acetyl transferase, luciferase, and the like. Preferably, the reporter gene is either the β-glucuronidase (GUS) gene or the luciferase gene. See, for example, Jefferson et al., *Plant Molecular Biology Reporter* 5(4):387 (1987). General descriptions of plant expression vectors and reporter genes can be found in Gruber et al., "Vectors for Plant Transformation," in METHODS IN PLANT MOLECULAR BIOLOGY AND BIOTECHNOLOGY, Glick et al. (eds.), pages 89–119 (CRC Press, 1993).

Moreover, GUS expression vectors and GUS gene cassettes are available from Clontech Laboratories, Inc. (Palo Alto, Calif.), while luciferase expression vectors and luciferase gene cassettes are available from Promega Corporation (Madison, Wis.).

Expression vectors containing test genomic fragments can be introduced into protoplasts, or into intact tissues or isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993). Methods of introducing expression vectors into plant tissue include the direct infection or co-cultivation of plant tissue with *Agrobacterium tumefaciens*. Horsch et al., *Science* 227:1229 (1985). Descriptions of Agrobacterium vector systems and methods for Agrobacterium-mediated gene transfer are provided by Gruber et al., supra, and Miki et al., supra. Methods of introducing expression vectors into plant tissue also include direct gene transfer methods such as microprojectile-mediated delivery, DNA injection, electroporation, and the like. See, for example, Gruber et al., supra; Miki et al., supra.

The above-described methods have been used to identify and characterize the Brassica ALS3 promoter that is constitutively expressed in transformed plants. In particular, the ALS3 constitutive and generally non-tissue-preferred promoter was found to reside within a 1063 bp DNA fragment shown in FIG. 1 [SEQ ID NO: 1]. Thus, the present invention encompasses a DNA molecule having a nucleotide sequence of SEQ ID NO: 1 and having the function of a constitutive plant promoter.

Variants of the 1063 bp generally constitutive and non-tissue-preferred promoter can be produced by deleting, adding and/or substituting nucleotides for the nucleotides recited in SEQ ID NO: 1. Such variants can be obtained, for example, by oligonucleotide-directed mutagenesis, linker-scanning mutagenesis, mutagenesis using the polymerase chain reaction, and the like. Ausubel et al., supra, at pages 8.0.3–8.5.9. Also see generally, McPherson (ed.), DIRECTED MUTAGENESIS: A PRACTICAL APPROACH, IRL Press (1991). Thus, the present invention also encompasses DNA molecules comprising nucleotide sequences that have substantial sequence similarity with SEQ ID NO: 1 and function as a tissue-general promoter.

Moreover, additional deletion analyses are performed to further localize the core promoter region within the 1063 bp promoter. Thus, the present invention also encompasses fragments of the DNA molecule having nucleotide sequence of SEQ ID NO: 1, as long as the DNA fragments function as a constitutive promoter.

IV. Vector Construction

The 1063 bp XbaI/NcoI fragment shown in FIG. 1 [SEQ ID NO: 1] was fused to a GUS reporter genes cassette which includes the 3-prime terminator sequence from the potato proteinass inhibitor genes (PINII). The ALS3 promoter was cloned as an XbaI/EcoRI fragment into the corresponding sites of the binary vector pPHI1741 to create plasmid pPHI4960 (FIG. 3). Plasmid pPHI1741 differs from plasmid pBI101.1, taught by Jefferson et al., supra, by having the CaMV 35S rather than the nopaline synthase 5-prime and 3-prime regulatory sequences driving the NPTII selectable marker gene.

Figure 4:
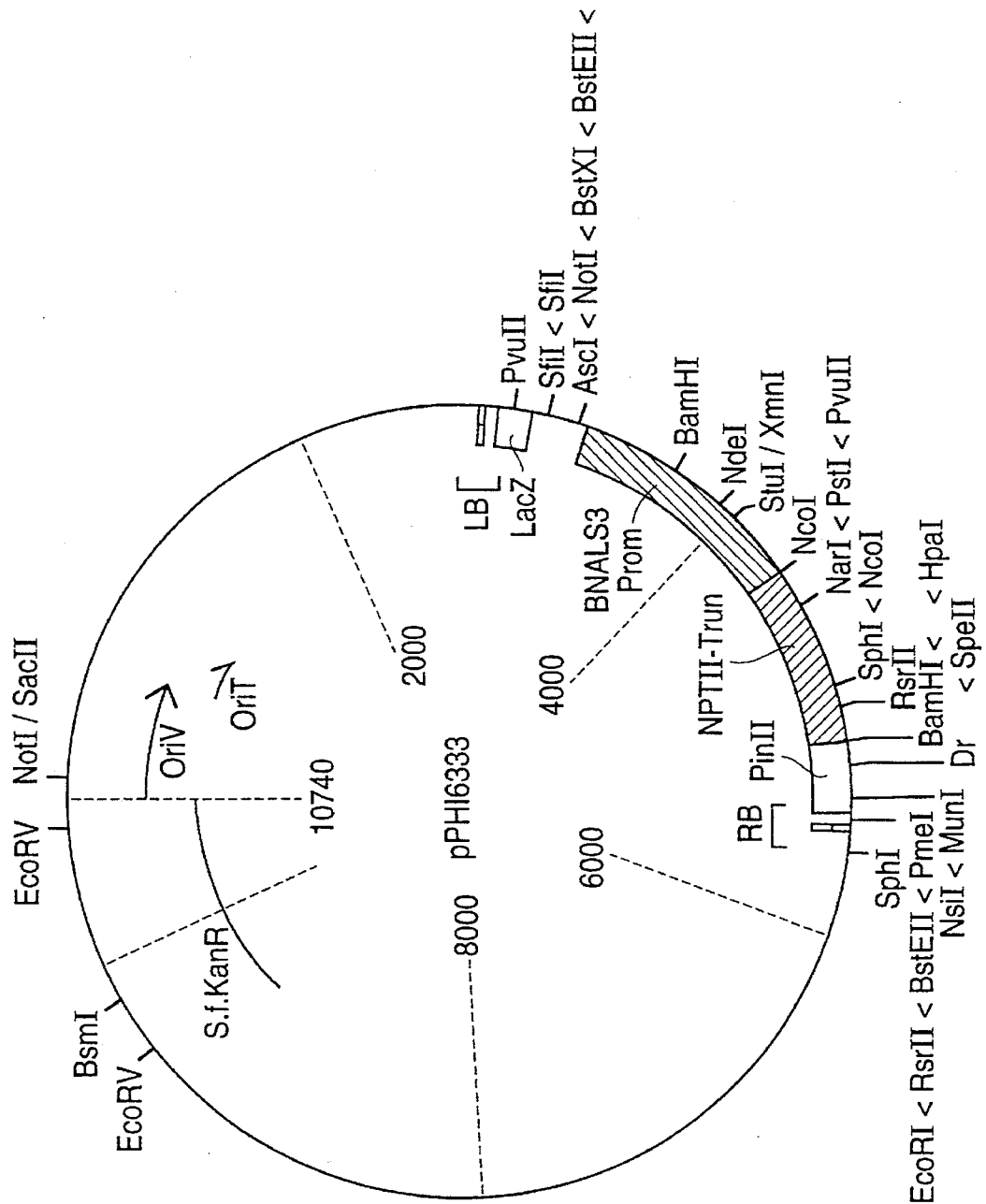
FIG. 4 presents a map of pPHI6333 which is a binary vector containing a cassette comprising the *B. napus* ALS3 promoter (BNALS3 PROM), NPTII gene and the 3-prime terminator sequence from the potato proteinase inhibitor gene (PINII). Plasmid pPHI6333 was used to transform sunflower to ascertain the suitability of this promoter for driving selectable marker expression. LB and RB represent the left and right borders, respectively, of the Agrobacterium Ti plasmid T-DNA region.

The vector pPHI6333 was constructed by replacing the region between the PmeI and EcoRI sites of pPHI1741 with a cassette containing the ALS3 promoter driving an NPTII selectable marker gene and the PINII 3' terminator sequence (FIG. 4).

V. Agronomic Genes and Selectable Marker Genes for Brassica Transformation

By means of the present invention, agronomic genes and selectable marker genes can be operably linked to the ALS3 promoter and constitutively expressed in transformed plants. More particularly, Brassica can be genetically engineered to express various phenotypes of agronomic interest. The genes implicated in this regard include, but are not limited to, those categorized below.

1. Genes That Confer Resistance To Pests or Disease And That Encode:

(A) Plant disease resistance genes. Plant defenses are often activated by specific interaction between the product of a disease resistance genes (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78.:1089 (1994) (Arabidopsis RSP2 gene for resistance to *Pseudomonas syringae*).

(B) A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection (Rockville, Md.), under ATCC accession Nos. 40098, 67136, 31995 and 31998.

(C) A lectin. See, for example, the disclosure by Van Damme et al., *Plant Molec. Biol.* 24:825 (1994), who disclose the nucleotide sequences of several *Clivia miniata* mannose-binding lectin genes.

(D) A vitamin-binding protein such as avidin. See U.S. patent application Ser. No. 07/911,864, now abandoned, the contents of which are hereby incorporated by reference. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), and Sumitani et al., *Biosci. Biotech. Biochem.* 57:1243 (1993) (nucleotide sequence of *Streptomyces nitrosporeus* α-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116:165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

(K) A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

(L) A hydrophobic moment peptide. See U.S. patent applications Ser. No. 08/168,809 (disclosure of peptide derivatives of Tachyplesin which inhibit fungal plant pathogens), now abandoned, and Ser. No. 08/179,632 (teaches synthetic antimicrobial peptides that confer disease resistance), now U.S. Pat. No. 5,607,914, the respective contents of which are hereby incorporated by reference.

(M) A membrane permease, a channel former or a channel blocker. For example, see the disclosure by Jaynes et al., *Plant Sci.* 89:43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

(P) A virus-specific antibody. See, for example, Tavladoraki et al., *Nature* 366:469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalac-turonase-inhibiting protein is described by Toubart et al., Plant J. 2:367 (1992).

(R) A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes That Confer Resistance To A Herbicide, For Example:

(A) A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

(B) Glyphosate (resistance imparted by mutant EPSP synthase and aroA genes, respectively) and other phosphono compounds such as glufosinate (PAT and bar genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricinacetyl-transferase gene is provided in European application No. 0 242 246 to Leemans et al. De Greef et al., Bio/Technology 7:61 (1989), describe the production of transgenic plants that express chimeric bar genes coding for phosphinothricin acetyl transferase activity. Exemplary of genes conferring resistance to phenoxy proprionic acids and cyclohaexones, such as sethoxydim and haloxyfop, are the Acc1-S1, Acc1-S2 and Acc1-S3 genes described by Marshall et al., Theor. Appl. Genet. 83:435 (1992).

(C) A herbicide that inhibits photosynthesis, such as a triazine (psbA and gs+ genes) and a benzonitrile (nitrilase gene). Przibilla et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC accession Nos. 53435, 67441 and 67442. Cloning and expression of DNA coding for a glutathione S-transferase is described by Hayes et al., Biochem. J. 285:173 (1992).

3. Genes That Confer Or Contribute To A Value-Added Trait, Such As:

(A) Modified fatty acid metabolism, for example, by transforming maize Brassica with an antisense gene of stearoyl-ACP desaturase to increase stearic acid content of the plant. See Knultzon et al., Proc. Nat'l Acad Sci. USA 89:2624 (1992).

(B) Decreased phytate content
(1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an Aspergillus niger phytase gene.
(2) A gene could be introduced that reduces phytate content. In maize, this, for example, could be accomplished, by cloning and then re-introducing DNA associated with the single allele which is responsible for maize mutants characterized by low levels of phytic acid. See Raboy et al., Maydica 35:383 (1990).

(C) Modified carbohydrate composition effected, for example, by transforming plants with a gene coding for an enzyme that alters the branching pattern of starch. See Shiroza et al., J. Bacteriol. 170:810 (1988) (nucleotide sequence of Streptococcus mutans fructosyltransferase gene), Steinmetz et al., Mol. Gen. Genet. 200:220 (1985) (nucleotide sequence of Bacillus subtilis levansucrase gene), Pen et al., Bio/Technology 10:292 (1992) (production of transgenic plants that express Bacillus licheniformis α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley amylase gene), and Fisher et al., Plant Physiol. 102:1045 (1993) (maize endosperm starch branching enzyme II).

4. Selectable Marker Genes:

(A) Numerous selectable marker genes are available for use in plant transformation including, but not limited to, neomycin phophotransferase I, hygromycin phophotransferase, EPSP synthase and dihydropteroate. See Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993).

Synthesis of genes suitably employed in the present invention can be effected by means of mutually priming, long oligonucleotides. See, for example, Ausubel et al. (eds.), CURRENT PROTOCOLS IN MOLECULAR BIOLOGY, pages 8.2.8 to 8.2.13 (Wiley Interscience 1990), and Wosnick et al., Gene 60:115 (1987). Moreover, current techniques which employ the polymerase chain reaction permit the synthesis of genes as large as 1.8 kilobases in length. See Adang et al., Plant Molec. Biol. 21:1131 (1993), and Bambot et al., PCR Methods and Applications 2:266 (1993).

The present invention, thus generally described, will be understood more readily by reference to the following examples, which are provided by way of illustration and are not intended to be limiting of the present invention.

Example 1

Plant Transformation and Expression Analysis

Figure 5:
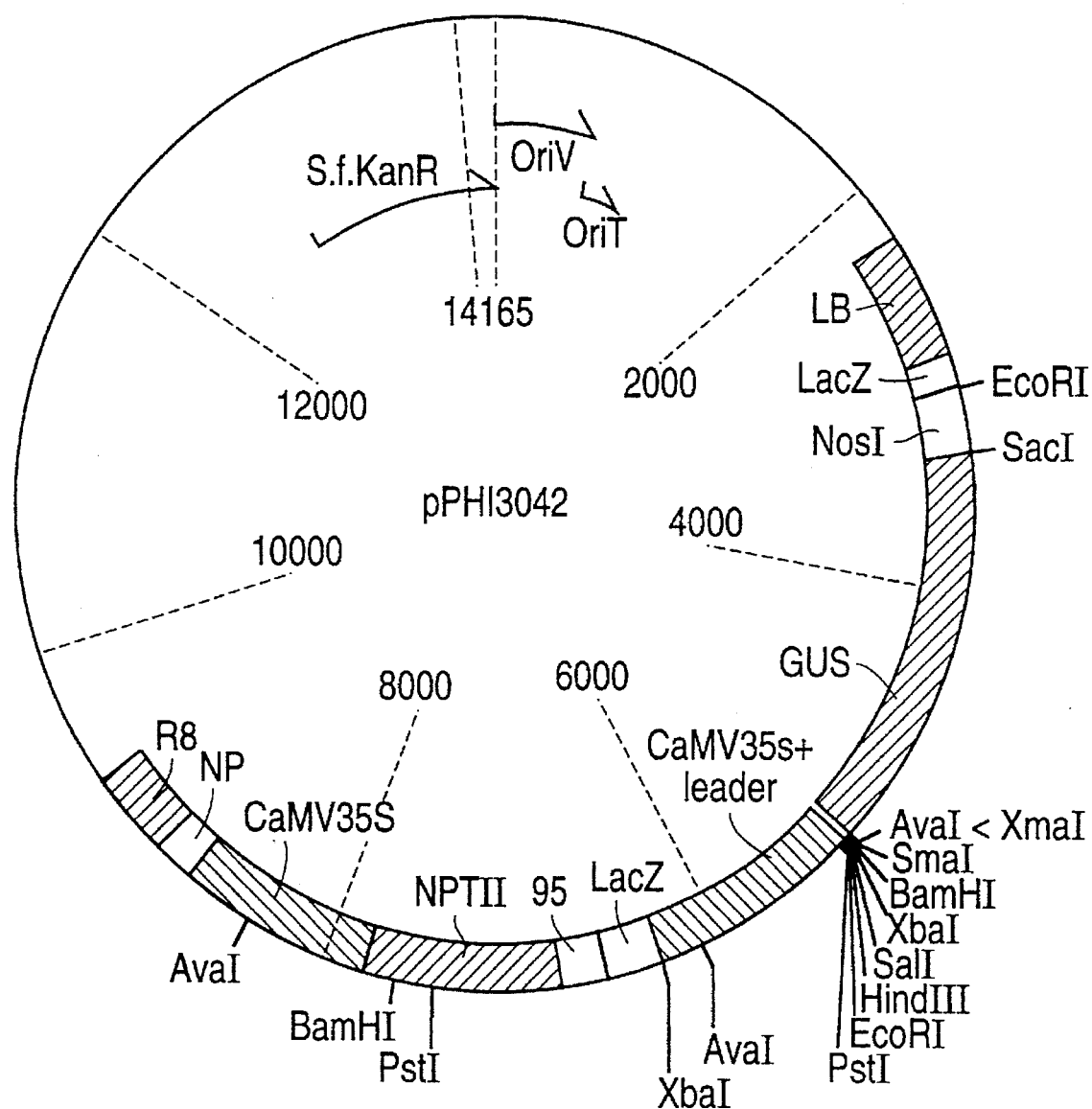
FIG. 5 presents a map of plasmid pPHI3042 which contains the NPTII and GUS structural genes operably linked to the CaMV 35S promoter.
Figure 6:
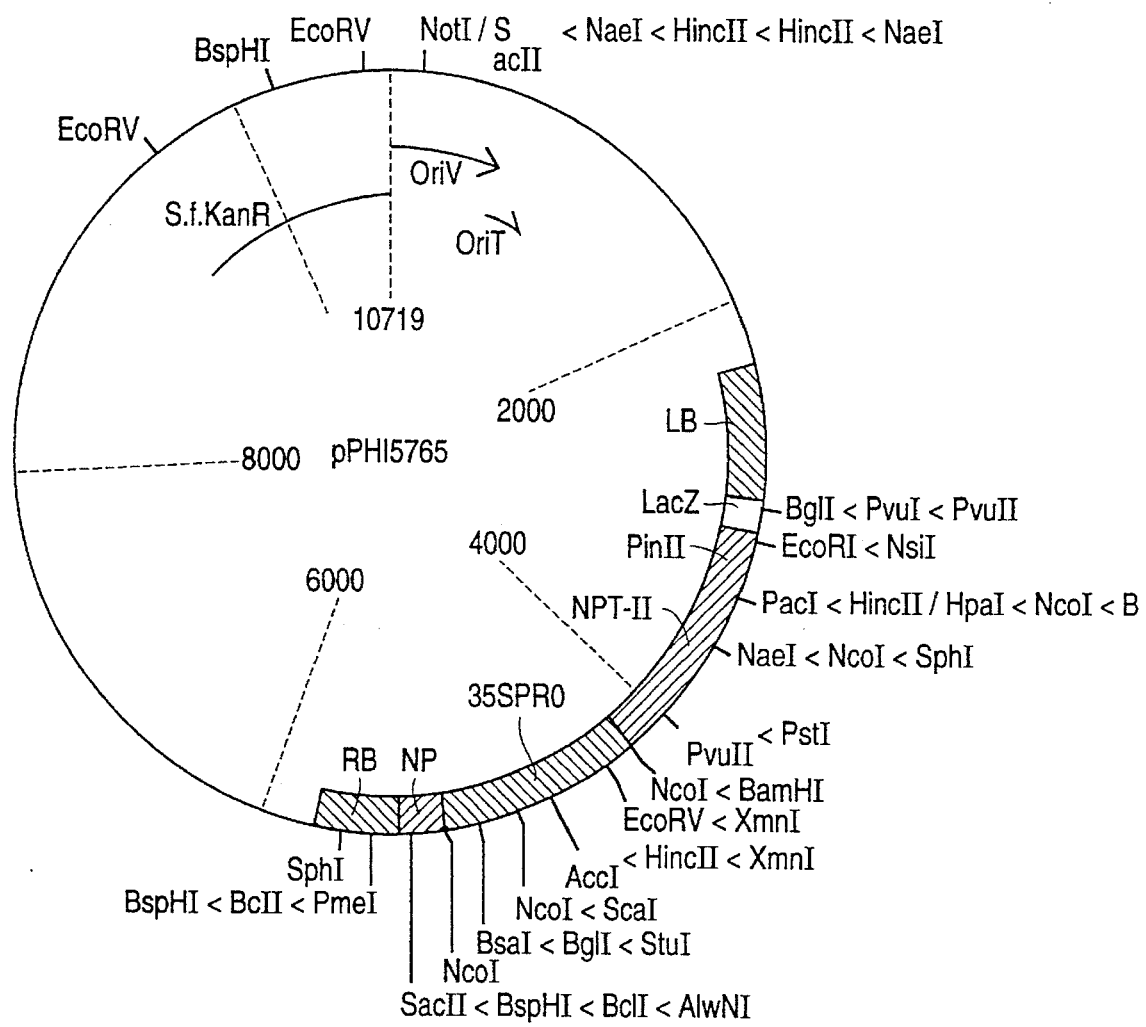
FIG. 6 presents a map of plasmid pPHI5765 which contains the NPTII structural gene operably linked to the CaMV 35S promoter (35SPRO) and the potato proteinase inhibitor gene terminator sequence (PINII).
Figure 7:
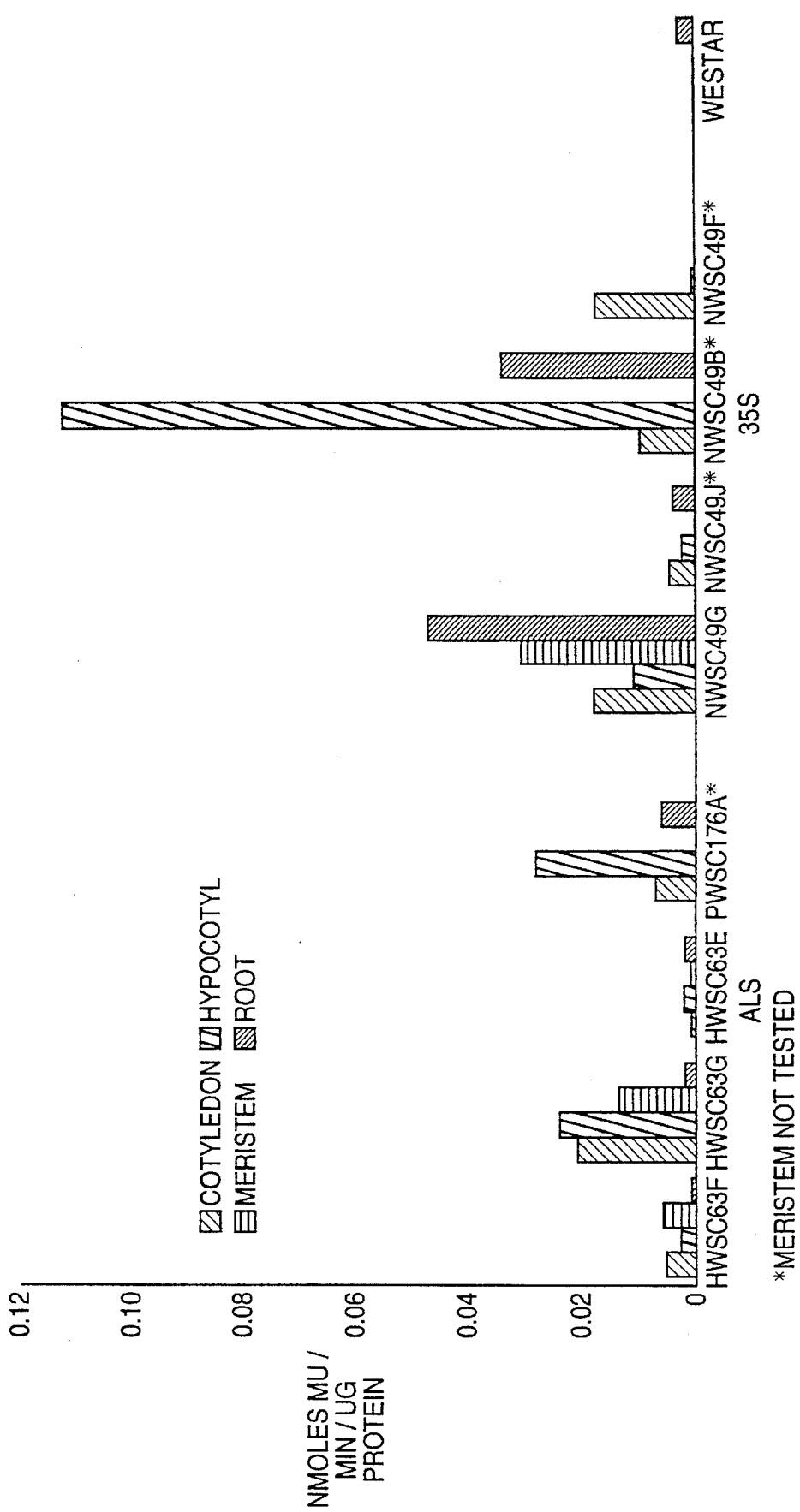
FIG. 7 is a histogram showing GUS activity in plant seedlings transformed with expression cassettes in which the GUS gene is expressed from either the CaMV 35S or ALS3 promoters. GUS activity was measured in cotyledon, hypocotyl, meristem and root tissues.

The vector pPHI4960, shown in FIG. 3, was introduced into the Agrobacterium strain GV3101 by transformation. B. napus cultivar Westar was used throughout this experiment. Transgenic B. napus plants were generated by Agrobacterium co-cultivation of cotyledonary petioles and microspore derived embryos. See Arnoldo et al., Genome 35:58 (1992). Parallel transformations were carried out using pPHI3042 in order to compare the strength of the ALS3 promoter with that of the CaMV 35S promoter. Plasmid pPHI3042 is shown in FIG. 5 and contains the CaMV 35S promoter operably linked to the GUS gene. Tissues from plants containing independent transformation events were quantitatively analyzed for GUS expression using a histochemical assay method based on that of Jefferson R. A., *Plant Mol. Biol. Rep.* 5:387 (1987).

Table 1 summarizes quantitative GUS expression data from *B. napus* plants independently transformed with plasmid pPHI4960 (HWSC63E, HWSC63F, HWSC63G, HWSC63H, PWSC174C, PWSC174D, PWSC174G, PWSC174J, PWSC174M, PWSC174N, and PWSC176A). Tissue from the primary transgenic plant (T0) was analyzed. Plasmid pPHI4960 is shown in FIG. 3 and contains the *B. napus* ALS3 promoter operably linked to the GUS gene. The controls consisted of the same nontransformed cultivar 'Westar' and 4 independent *B. napus* plants transformed with the plasmid pPHI3042 (P105B, P105E, P126B and P145).

TABLE 1

SUMMARY OF BRASSICA NAPUS TRANSFORMED WITH pPHI4960 AND pPHI3042

| Transgenic | GUS Expression (T0) Fluorogenic (pmoles/MU/h/µg protein) | | Southern PINII Probe |
|---|---|---|---|
| | leaf | root | |
| HWSC63E[1] | 0.2 | 6.2 | 5 |
| HWSC63F[1] | 131 | 167 | 1 |
| HWSC63G[1] | 416 | 246 | 1 |
| HWSC63H[1] | 21 | 29 | 1 |
| PWSC174C[1] | 7.5 | 63.6 | 1 |
| PWSC174D[1] | 11 | 17 | 1 |
| PWSC174G[1] | 309 | no root | 0/1 |
| PWSC174J[1] | | | 1 |
| PWSC174M[1] | | | 0/1 |
| PWSC174N[1] | | | 1 |
| PWSC176A[1] | 0.2 | 37 | 4 |
| P105B[2] | 316 | 143 | |
| P105E[2] | 241 | 279 | |
| P126B[2] | 0.4 | 1.2 | |
| P145[2] | 0.2 | 0.6 | |
| WESTAR[3] | 0.1 | 11.2 | |

[1]*B. napus* transformed with pPHI4960
[2]*B. napus* transformed with pPHI3042
[3]Non-transgenic control The data reveal that there is variability in the level of expression in the transformants. Variability in the level of expression of transformed genes has been noted in numerous transformation experiments described in the literature and has been attributed to such factors as differences in copy number, position effects and co-suppression. However, plants expressing high levels, or a desired level, of the foreign protein can be identified and selected using the routine screening methods of the present invention.

The data also reveal that there are essentially two classes of expression levels in plants transformed with plasmid pPHI4960. The first class consists of transformed plants expressing high levels of assayable product (131–416 pmol of methylumbelliferone (MU)/h/µg protein). The second class consists of transformed plants expressing low levels of assayable product (0.2–37 pmol MU/h/µg protein). The low expression level is generally comparable to the nontransformed control plants examined. These values do not imply absolute expected ranges but represent the maximum and minimum values for each class in the present study.

Southern blot analysis of total genomic DNA isolated from transformed plants was undertaken to determine the copy number of the GUS gene cassette in each transformant. The PINII terminator was used as the radiolabeled hybridization probe. Total genomic DNA was isolated from each plant transformant using a variation of a CTAB protocol. See, for example, Dellaporta et al., 1983, *Plant Mol. Biol. Rep.* 1(4):19–21, or Saghai-Maroot et al., 1984, *PNAS* 8:8014–8018. The total genomic DNA was digested with a restriction enzyme(s), separated on agarose gels by means of electrophoresis and hybridized with the radiolabeled PINII terminator sequence as a probe. Plasmid pPHI4960 was digested with either HindIII alone to assess number of integrations, or double digested with HindIII plus EcoRI to determine copy number. Similarly, pPHI3042 was digested with HindIII alone to assess number of integrations, or with EcoRI alone to evaluate copy number (see enzyme cut sites on maps in FIGS. 3 and 5, respectively). Although an exact copy number for each integration event was not determined, the relative intensities of hybridizing bands were used to compare Southern data between transgenics with different vectors.

Plants transformed with multiple copies of the plasmid pPHI4960 (HWSC63E and PWSC176A) produced low levels of MU. On the other hand, 50% of the single integration events produced high levels of MU. Plants with single transformation events produced high levels of MU irrespective of whether the GUS gene was expressed from the CaMV 35S or the ALS3 promoter.

Among the transformed plants producing high levels of MU, plants transformed with the ALS3 GUS cassette produced just as much MU as plants transformed with the CaMV 35S GUS cassette, irrespective of whether enzyme activity was measured in the roots or shoots. Since the CaMV 35S promoter is regarded as a strong constitutive, generally non-tissue-preferred promoter, with wide application in expressing genes in transgenic plants, the Brassica ALS3 promoter offers a suitable alternative to the CaMV 35S promoter.

The level of GUS expression measured in leaf tissue of HWSC63G was higher than the GUS level produced in leaf or root tissue of plants transformed with the CaMV 35S GUS cassette. Accordingly, the ALS3 promoter may be more effective than the CaMV 35S promoter for expression of certain genes at high levels. For example, the ALS3 promoter may be preferable to the CaMV 35S promoter in those instances where high level expression of the transformed gene is required. It is understood by those skilled in the art that the range of expression in transgenic plants can vary among transformation events. The present data indicates that it is possible to recover at least some events with activity comparable to that obtained with the 35S promoter by means of routine screening using the methods disclosed herein. To test the usefulness of the ALS3 promoter for expression of operably linked genes in other species, transformations were also conducted in sunflower. Sunflower leaf discs were co-cultivated with Agrobacterium carrying either pPHI4960 or pPHI6333. See Malone-Schoneberg, et al., 1994, *Plant Science* 103: 199–207. Stably transformed calli were selected using 100 mg/L of kanamycin. GUS or NPTII expression levels were determined for a number of independent transformation events, using histochemical staining for GUS expression analysis, and semi-quantitative ELISAs for NPTII expression analysis. While GUS expression varied among individual plants, the ranges of expression from the two promoters in leaf tissues overlapped substantially (73-3119 fluorescence units for the ALS3 promoter and 40-2788 fluorescence units for the 35S promoter). Limited ELISAs also yielded comparable results for NPTII expression from the two promoters (data not shown), although extensive whole plant analysis was not carried out.

Example 2

Activity of the ALS3 Promoter in Transgenic *B. napus* in Selected Tissues from Seedling, Vegetative, Flowering and Mature Stage Plants

*B. napus* cv. Westar was transformed with pPHI4960 as described in Example 1. Four independent transformants were analyzed (HWSC63F, HWSC63G, HWSC63E and PWSC176A). The primary transformants are designated T0. The seed produced by T0 plants are T1 seeds and the plants produced by T1 seeds are referred to as T1 plants.

GUS expression was quantitatively determined, by the method described in Example 1, in T1 plants at the seedling stage (less than 2 true leaves), the vegetative stage (4–5 true leaves), the early flowering stage (about 20–80% full bloom), and in mature plants. In addition, GUS expression was quantitatively determined in specific plant tissues, including meristem, cotyledon, hypocotyl, leaf, petiole, stem, root, pod, seed and flowers. "Meristem" refers to the meristematic apex and includes much of the tissue surrounding the true meristem. "Flowers" refers tO all organs associated with the flowers, including ovaries, anthers and petals. "Pods" refers to the developing green pods containing green and brown seed. "Seed" refers to the seed still on the plant, hence the seeds were not desiccated. The results of quantitative enzyme assays were confirmed by means of histochemical assays as in example 1.

GUS expression in B. napus cv. Westar transformed with pHI4960 was compared to plants of the same cultivar transformed with pPHI3042. A non-transgenic Westar line was used as a control. Although T1 stage plants are segregating with respect to the transformed genes, only T1 plants that had a transgene, as evidenced by expression of neomycin phosphotransferase or survival on kanamycin, were analyzed. Seeds were sown on an agar plate containing 100 μg/ml of kanamycin. Those seeds which germinated and resulted in green seedlings were selected as transformed segregants. Those which bleached white were non-transformed segregants and were discarded or used as negative controls.

Figure 8:
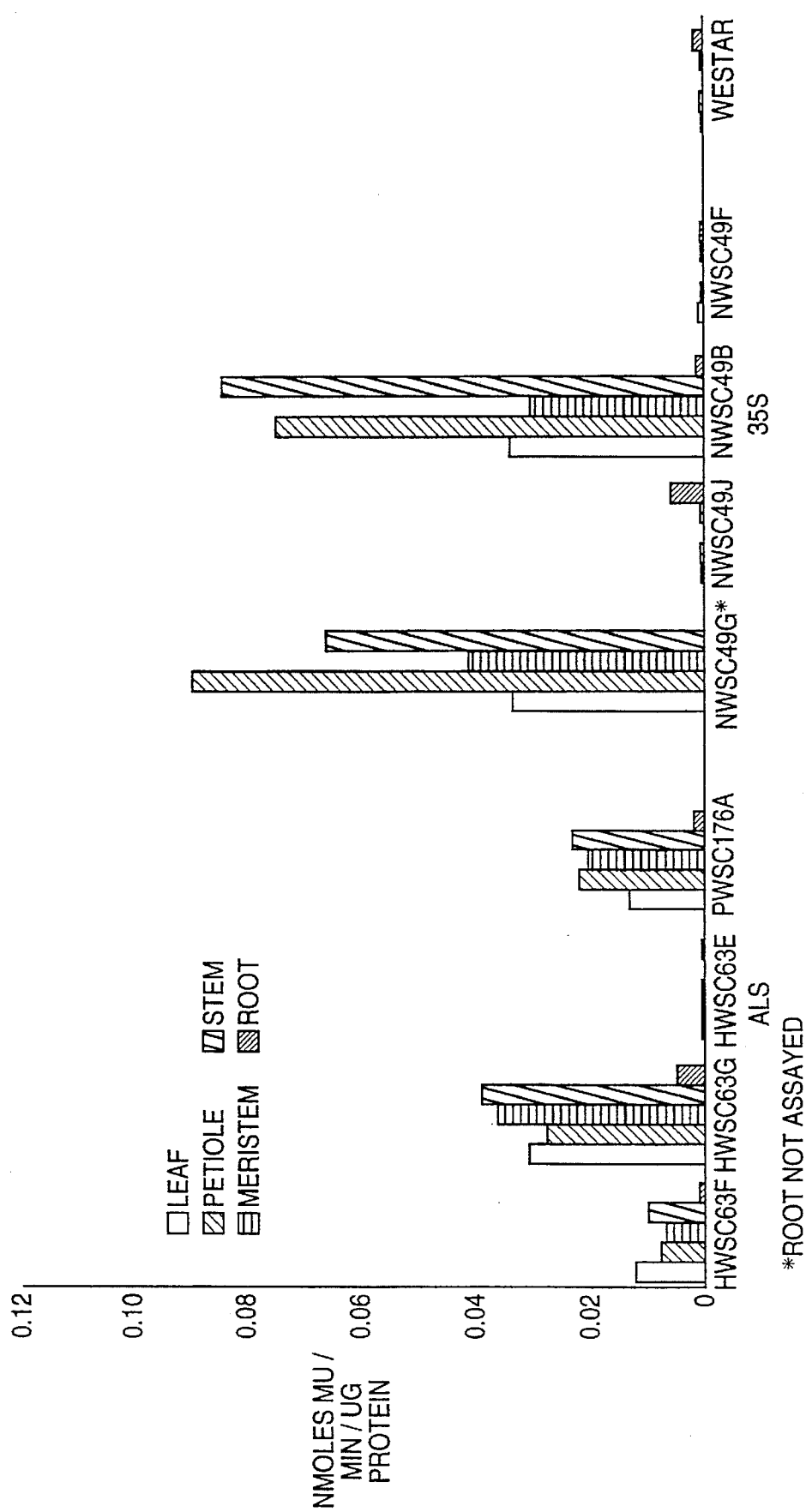
FIG. 8 is a histogram showing GUS activity in vegetative stage plants transformed with expression cassettes in which the GUS gene is expressed from either the CaMV 35S or ALS3 promoters. GUS activity was measured in leaf, petiole, meristem, stem and root tissues.
Figure 9:
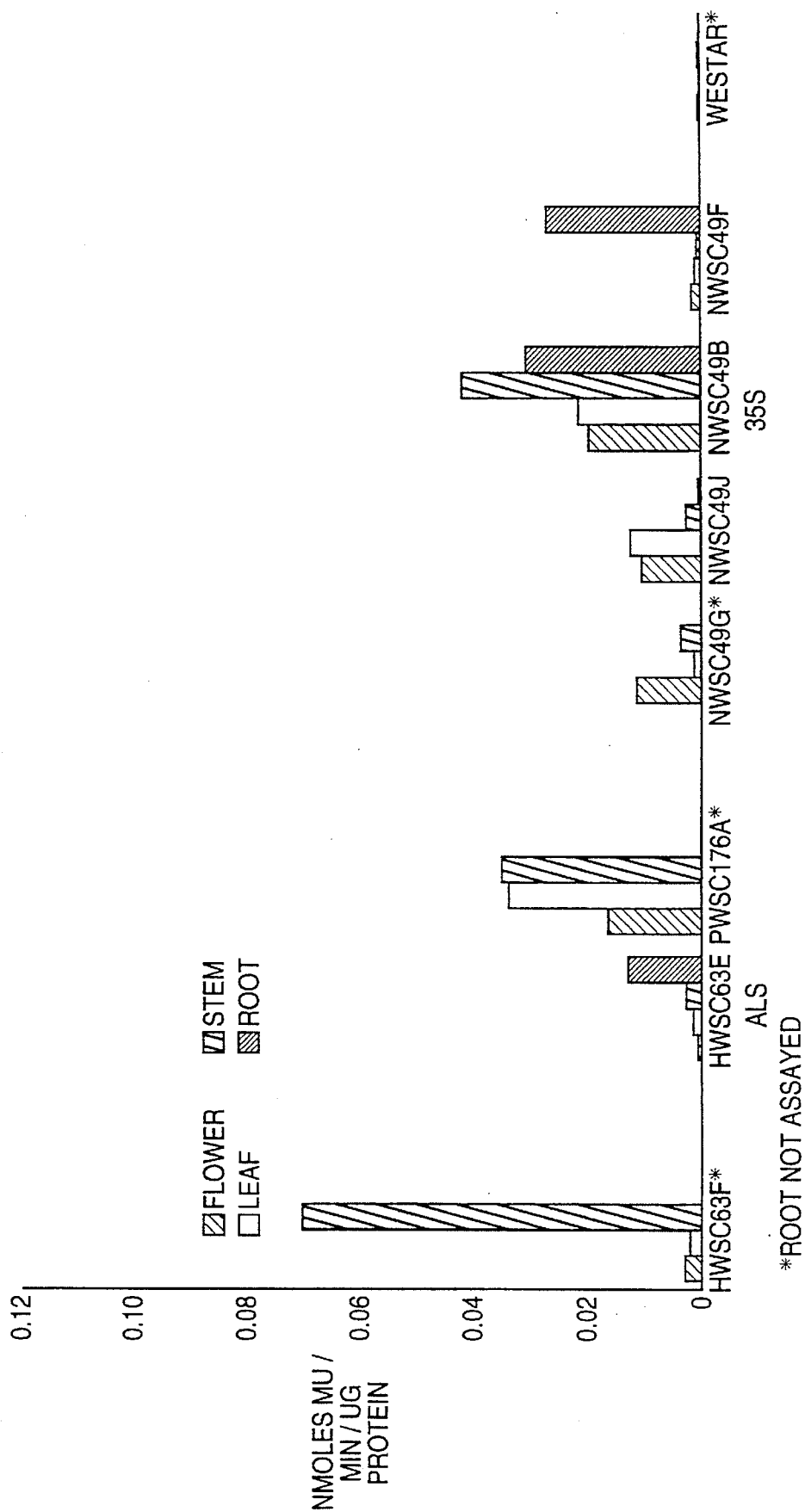
FIG. 9 is a histogram showing GUS activity in flowering stage plants transformed with expression cassettes in which the GUS gene is expressed from either the CaMV 35S or ALS3 promoters. GUS activity was measured in flower, leaf stem and root tissues.
Figure 10:
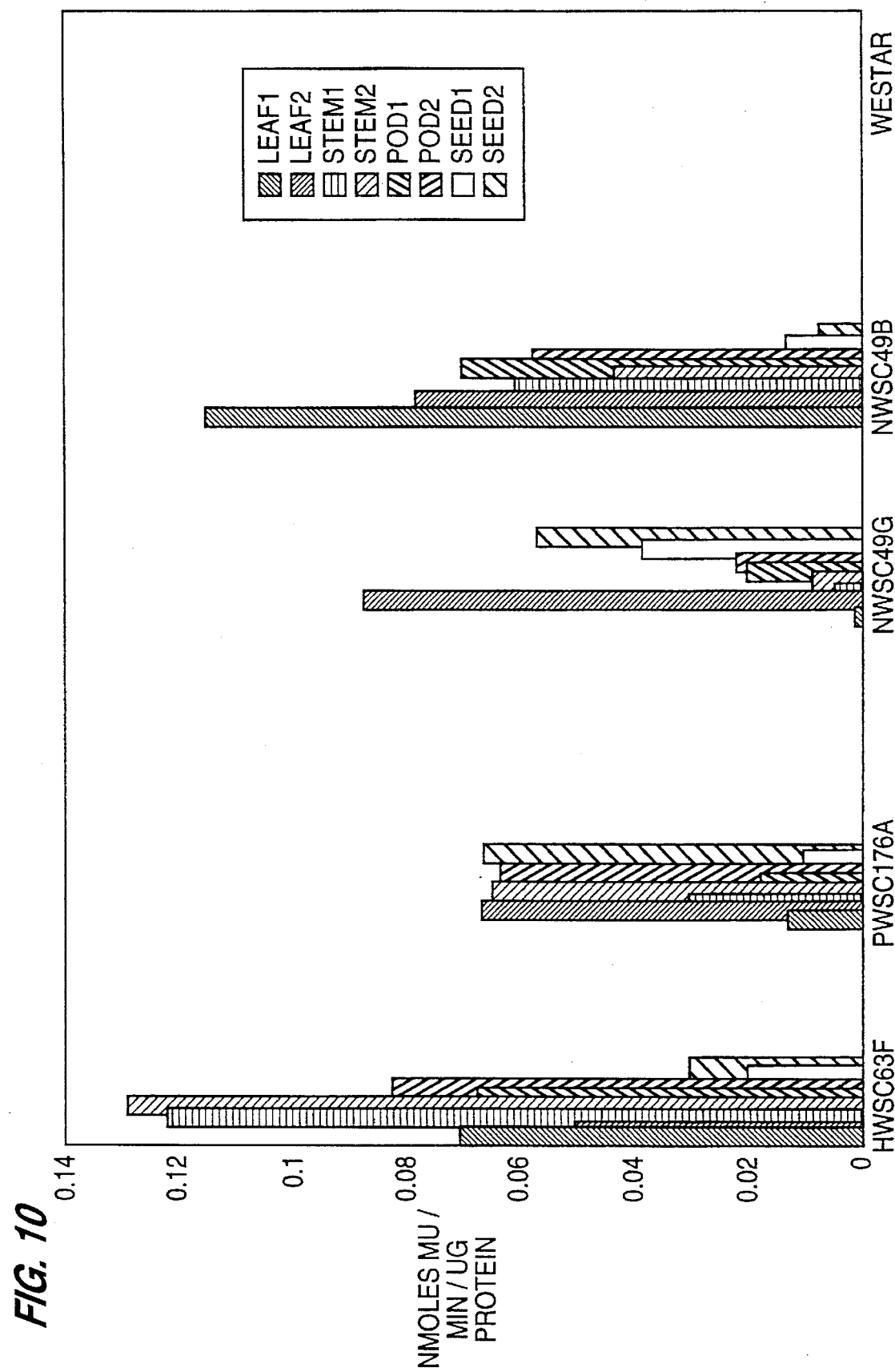
FIG. 10 is a histogram showing GUS activity in mature plants transformed with expression cassettes in which the GUS genes is expressed from either the CaMV 35S or ALS3 promoters. GUS activity was measured in leaf, stem, pod and seed tissues.

Table 2 summarizes Southern, expression and segregation data for several transgenics. GUS expression was measured in leaf tissue from plants at the 3–7 leaf stage. In those primary transgenics with a simple integration pattern, which either showed no segregation (and were therefore fixed) or whose subsequent progeny segregated in approximately a 3:1 ratio with respect to the transformed genes, the levels of GUS expression from both the 35S and ALS3 promoters was relatively high. In contrast, those with complex integration patterns and/or with complex segregation had low GUS expression.

seedlings, specifically in cotyledons, hypocotyls and "meristematic apex." The ALS3 promoter drives low level expression of GUS in the roots at the seedling stage. At the 4–5 true leaf stage, the ALS promoter functions in leaves, petioles, stem, "meristematic apex" and roots, as shown in FIG. 8. At the flowering stage, the ALS3 promoter functions in flowers, leaves, stem and roots (FIG. 9). Histochemical analysis of flowers revealed expression of GUS in petals, stigma, anthers and pollen. GUS activity was detected in all tissues (leaf, stem pod and seed) taken from mature B. napus plants transformed with pPHI4960. Accordingly, the ALS3 promoter is constitutively expressed in diverse plant tissues throughout the development of the plant.

Example 3

Selectable Marker Genes Expressed from the ALS3 Promoter

The ALS3 promoter can be used to drive expression of selectable marker genes for plant transformation. B. napus was transformed with plasmids pPHI1741, pPHI3042, pPHI5765 and pPHI6333 (FIG. 4) using the methods described in Example 1. Transformants were selected on medium containing 100 μg/ml kanamycin. Plasmid pPHI1741 contains the CaMV 35S promoter operably linked to the NPTII structural gene and the terminator sequence of the 195 gene. Plasmid pPHI3042 contains two expression cassettes with the CaMV 35S promoter operably linked to the NPTII structural gene and the CaMV 35S promoter operably linked to the GUS gene. Plasmid pPHI5765 contains the CaMV 35S promoter operably linked to the NPTII structural gene. Finally, plasmid pHI6333, shown in FIG. 4, contains the ALS3 promoter operably linked to the NPTII structural gene and the terminator sequence of the potato proteinase inhibitor gene (PINII).

TABLE 2

ALS Promoter Study

| | Southern (T0) | T0 GUS assay results | T1 GUS assay results | Segregation |
|---|---|---|---|---|
| 35S Transgenics | | | | |
| NWSC49J | 8 INSERTS | LOW | LOW | 23:1 |
| NWSC49B | 1 INSERT | HIGH | HIGH | 3:1 (18:6) |
| NWSC49F | 1 INSERT | MEDIUM | LOW | 3:4 |
| dhNWSC49G | 2 INSERTS | MEDIUM | HIGH/MED | 14:0 (FIXED) |
| ALS Transgenics | | | | |
| PWSC176A | 4 INSERTS | MEDIUM | HIGH | 4:1 (16:4) |
| HWSC63B | 5 INSERTS | LOW | LOW | 2:1 (9:5) |
| HWSC63F | 1 INSERT | HIGH | MED/HIGH | 7:1 (14:2) |
| HWSC63G | 1 INSERT | HIGH | HIGH | 7:0 |

FIGS. 7, 8, 9 and 10 present GUS expression data in specific tissues taken from plants at the seedling, vegetative, flowering and mature stage, respectively. As evidenced by the results shown in FIG. 7, the ALS3 promoter functions in

TABLE 3

Selectable Marker Genes Expressed From the ALS3 Promoter

| VECTOR | TOTAL NUMBER OF EXPLANTS COCULTIVATED | TOTAL NUMBER OF POSITIVES | PERCENT TRANS-FORMED |
|---|---|---|---|
| pPHI1741 | 1350 | 64 | 4.7% |
| pPHI3042 | 350 | 2 | 0.9% |
| pPHI5765 | 1935 | 60 | 3.1% |
| pPHI6333 | 1935 | 12 | 0.6% |

As shown in Table 3, the ALS3 promoter is effective in driving expression of the NPTII selective marker gene in canola. Transformation of plasmids pPHI1741, pPH3042 and pPHI5765 resulted in the recovery of 4.7%, 0.9% and 3.1% transformants among the total *B. napus* explants cocultivated with these plasmids, respectively. A total of 12 transformants were obtained from experiments in which pPHI6333 was cocultivated with 1,935 *B. napus* explants, or 0.6% of the explants were transformed. Ten of the 12 transformants expressed low levels of NPTII. In sunflower, pPHI6333 was as effective as pPHI4960 for selection of transformed plants; that is, both the 35S and the ALS3 promoter allowed selection of transformed tissues at 100 mg/L of kanamycin. Accordingly, the ALS3 promoter is effective in driving expression of a selective marker gene for plant transformation.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. An isolated DNA molecule comprising a promoter operably linked to a foreign structural gene, wherein said promoter comprises a nucleotide sequence which is a XbaI/NcoI fragment 5-prime to the *Brassica napus* ALS3 structural gene.

2. An isolated DNA molecule comprising a promoter operably linked to a foreign structural gene, wherein said promoter comprises a nucleotide sequence which is SEQ ID NO: 1.

3. The DNA molecule of claims 1 or 2, wherein said foreign structural gene is an agronomically important gene or a selectable marker gene.

4. An expression vector comprising the isolated DNA molecule of claim 1.

5. An expression vector comprising the isolated DNA molecule of claim 2.

6. A transformed host comprising the expression vector of claim 4.

7. The transformed host comprising an expression vector of claim 5.

8. A method of using an ALS3 promoter to produce a foreign protein in a transformed host plant, comprising the steps of:
   (a) constructing an expression vector comprising a promoter operably linked to a foreign structural gene, wherein said promoter comprises a nucleotide sequence which is a XbaI/NcoI fragment 5-prime to the *Brassica napus* ALS3 structural gene; and
   (b) transforming said host plant.

9. A method of using an ALS3 promoter to produce a foreign protein in a transformed host plant, comprising the steps of:
   (a) constructing an expression vector comprising a promoter operably linked to a foreign structural gene, wherein said promoter comprises a nucleotide sequence which is SEQ ID NO: 1; and
   (b) transforming said host plant.

10. An isolated DNA molecule comprising a promoter operably linked to a foreign structural gene, wherein said promoter comprises a *Brassica napus* ALS3 structural gene promoter.

11. A method of using an ALS3 promoter to produce a foreign protein in a transformed host plant, comprising the steps of:
   (a) constructing an expression vector comprising a promoter operably linked to a foreign structural gene, wherein said promoter comprises a *Brassica napus* ALS3 structural gene promoter; and
   (b) transforming said host plant.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1063 base pairs
( B ) TYPE: nucleic acid
( C ) STRANDEDNESS: single
( D ) TOPOLOGY: linear ( x i ) SEQUENCE DESCRIPTION: SEQ ID NO:1:

```
TCTAGATTAA CATATGCGAC CACTCAGGTT AATAATTCTC CCAAATAACA TACATTGGTA      60

TGAAGATTAT GTCTAAATCA AACATAAAAT CGACTCCAAA TACGAACCCA CAAACTTACA     120

AGTAAATCAA ACATAAAATT TATCTGCATC CGACTATGTC TACGCCATTG TTTCACCACT     180

CACCAATTAT AGAGGGACAA ACCTACAGAT CATACTATAT CTAACAGATT TCAACCCCTA     240

AGCAATTCAC AGAATTGACA TGGACATAGC TAGAGCAAAC CTGCATGATG AAAGAAGGGC     300

ACCCACAGTG GCGGAAAAAG ATGAACTTTT GACAATACAC ATTGACAAGA TTGTATGAAG     360

TGGGGTTATA AATTCATTGC AATGCAATCA TATCTATCAT CACCAGTTCA TAATTGACTG     420

GATCCGAATG AACATAAGAT GCTCTACATG TCGAGACACA ATACTTTAGT CATAATGTTT     480

CTCATTATCA AGTACAGGTA TTTCTACTTT AAACTTATAT TATAAGCAAG TATTACAAAT     540

AATGAAATAA AGACTATGTT TTCCTGTTTT AGATGTTTCG ATCTTCATAT TTTAACCAAT     600

CGTCTTCATT ATTGCAAGAA ACACAATTTC CTAACTCCTG TAACACTCCT TATAAAAATA     660

TATGACATAT GAAACGGAGC GGAGGCTTGC AGTAGACGTA ACAACATTTT AAAATTGAAC     720

AAAGTATTGC TTAAAAAATA GAATTTGAAG GCCTTCTAAG CTGAACATAA AATAAAATTA     780

ACACAAAATT ATATCTTTCA TCACAACCAA CTGAACATAA AATAAAATTA ACACAAAATT     840

ATATCTTTCA TAAAAACCGA TACATCAAAT TCCGCGCGTA GCGCGGACCC TCCCTAGTAA     900

TTAATACAGT AAAGAAAAGA CCAAACAAAC AAAAATCATA TTCCAAGGGT ATTTTCGTAA     960
```

```
ACAAACAAAA CCCTCACAAG CCTCGTTTTA TAAAAACGAT TCACGTTCAC AAACTCATTC    1020

ATCATCTCTC TCTCATTTCT CTCTCTCTCT CATCTAACCA TGG                      1063
```